(12) United States Patent
Muto et al.

(10) Patent No.: US 10,052,172 B2
(45) Date of Patent: Aug. 21, 2018

(54) MAINTENANCE CHECKING SYSTEM AND METHOD FOR DENTAL HANDPIECE, AND SYSTEM AND METHOD FOR CONTROLLING DRIVE MOTOR

(71) Applicants: Shinichirou Muto, Kanuma (JP); Masaru Ishijima, Kanuma (JP); Keita Yokochi, Kanuma (JP); Hayato Matsushita, Kanuma (JP); Yukihiro Ueki, Kanuma (JP)

(72) Inventors: Shinichirou Muto, Kanuma (JP); Masaru Ishijima, Kanuma (JP); Keita Yokochi, Kanuma (JP); Hayato Matsushita, Kanuma (JP); Yukihiro Ueki, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 0 days.

(21) Appl. No.: 14/748,899

(22) Filed: Jun. 24, 2015

(65) Prior Publication Data
US 2015/0377969 A1 Dec. 31, 2015

(30) Foreign Application Priority Data
Jun. 25, 2014 (JP) .................................. 2014-129780

(51) Int. Cl.
*G01R 31/34* (2006.01)
*A61C 1/00* (2006.01)
(52) U.S. Cl.
CPC ............ *A61C 1/003* (2013.01); *G01R 31/343* (2013.01)
(58) Field of Classification Search
CPC ........ G01R 31/34; G01R 31/343; A61C 1/003

USPC ....................................................... 324/765.01
See application file for complete search history.

(56) References Cited

U.S. PATENT DOCUMENTS

| 6,955,536 | B1* | 10/2005 | Buchanan | A61C 1/0015 |
| | | | | 433/27 |
| 2004/0209223 | A1* | 10/2004 | Beier | A61B 17/1626 |
| | | | | 433/99 |
| 2008/0014550 | A1* | 1/2008 | Jones | A61C 1/0015 |
| | | | | 433/114 |

(Continued)

FOREIGN PATENT DOCUMENTS

JP 8-308858 A 11/1996

OTHER PUBLICATIONS

Misuaki, JP 3683305 Machine Translation, p. 1-9.*

*Primary Examiner* — Patrick Assouad
*Assistant Examiner* — Haidong Zhang
(74) *Attorney, Agent, or Firm* — Jason D. Voight

(57) ABSTRACT

A method for maintenance checking of a dental handpiece is disclosed. The method comprises measuring in advance no-load current values of a drive motor, with a handpiece known as being in usable condition and a handpiece known as insufficiently maintained respectively connected thereto and operated in no-load condition, storing as reference data the no-load current values of the drive motor together with associated data relating to degree of maintenance, measuring a no-load current value of the drive motor with a dental handpiece to be checked connected thereto and operated in no-load condition, and determining whether the handpiece checked is usable, requires maintenance, or is unusable, by comparing the measured no-load current value with the reference data.

4 Claims, 8 Drawing Sheets

(56) References Cited

U.S. PATENT DOCUMENTS

2014/0134565 A1* 5/2014 Kunisada ............ A61C 1/0007
433/27

* cited by examiner

MAINTENANCE CHECKING SYSTEM AND METHOD FOR DENTAL HANDPIECE, AND SYSTEM AND METHOD FOR CONTROLLING DRIVE MOTOR

This application claims priority to Japanese Patent Application No. 2014-129780, filed Jun. 25, 2014, the entire disclosure of which is hereby incorporated by reference herein.

FIELD OF ART

The present invention relates to maintenance checking system and method for a dental handpiece, that are intended for protecting a dental handpiece, such as a motor-driven, straight or contra-angle handpiece, from damages caused by heat generation in high-speed rotation due to insufficient maintenance of the handpiece, as well as system and method for controlling a drive motor for a dental handpiece.

BACKGROUND ART

In the art of dentistry, a dental handpiece is attached to and driven by a motor, of which rotation is transmitted through a train of gears to a dental tool, such as a cutting bur, at the tip of the handpiece for cutting teeth. There are a variety of trains of gears, such as for multiplying the rotation speed up to five times, transmitting the rotation at a direct ratio, or reducing the rotation speed. For example, in a handpiece having a gear train increasing the speed up to five times, the rotation speed of a motor at 40000 rpm is increased into the rotation speed of a bur at as high as 200000 rpm (five times) for cutting teeth. With a dental tool rotating at as such a high speed as 200000 rpm, proper maintenance, such as cleaning or lubricating, of the dental tool keeps the handpiece from abnormal heat generation, but absence of proper maintenance may result in attachment of dust or contaminants, or lubricant shortage in the driving section of the handpiece, including gears and bearings, which may cause abnormal heat generation.

In order to protect a dental handpiece from abnormal heat generation, a control technique is proposed, for example, in JP H08-308858. This publication discloses an electrical motor controlling system having a protection mechanism which warns that the current work is overloading when the micromotor is loaded so heavily as to generate heat to threaten its motor life, but still allows normal operation when the overloading is ceased.

Such an electrical motor controlling system detects the load of the micromotor during actual treatment of a patient, i.e., the load during tooth cutting, generates warning, and operates to suppress heat generation by the micromotor. However, this system cannot inform the user, before starting the operation, whether the handpiece parts connected to the micromotor are properly maintained, or the handpiece is appropriate for use, so that the user cannot decide whether to do the maintenance of the handpiece or not.

SUMMARY OF THE INVENTION

The present invention has been made to overcome the above problems. It is an object of the present invention to provide maintenance checking method and system for a dental handpiece, and a method and system for controlling a drive motor for a dental handpiece, which can determine, before actual operation of the handpiece, whether the handpiece has been maintained properly for work or not.

It is another object of the present invention to provide method and system for controlling a drive motor for a dental handpiece which, even when an improperly maintained dental handpiece is used, controls a drive motor for the dental handpiece in accordance with the determination made by the system or method mentioned above, without causing troubles such as generation of abnormal heat in the handpiece.

According to the present invention, there is provided a method for maintenance checking of a dental handpiece, comprising:

measuring in advance no-load current values of a drive motor, with a handpiece known as being in usable condition and a handpiece known as insufficiently maintained respective connected thereto and operated in no-load condition, storing as reference data said no-load current values of the drive motor together with associated data relating to degree of maintenance, measuring a no-load current value of the drive motor with a dental handpiece to be checked connected thereto and operated in no-load condition, and determining whether the handpiece checked is usable, requires maintenance, or is unusable, by comparing the measured no-load current value with said reference data.

As used herein, "maintenance check" is a process for determining whether the mechanical parts, including gears and bearings, of a handpiece have undergone proper maintenance, such as lubricating, for optimal condition.

As used herein, "no-load" means that a dental handpiece, and thus a dental tool attached in the tip thereof, is not cutting anything and not loaded. Thus "no-load current value" is the value of the current of the drive motor derived from the gear transmission loss in the handpiece when the handpiece is operated in the no-load condition, and is also termed as "transmission loss current value" hereinbelow.

According to an example of the present method, the no-load current value of the drive motor may be measured by measuring a current value of the drive motor with a handpiece connected thereto and operated in no-load condition, and subtracting a current value of the drive motor measured alone without a handpiece connected thereto, from the current value of the drive motor measured with a handpiece connected thereto.

According to an example of the present method, the reference data may further comprise a threshold $M1$ of the no-load current value up to which the handpiece is determined as usable, and a threshold $M2$ of the no-load current value beyond which the handpiece is determined as unusable, said thresholds $M1$ and $M2$ corresponding limits of an amount of heat generated by the handpiece with respect to the no-load current value of the drive motor measured in advance based on a relation therebetween, and wherein in said determining, the handpiece is determined as being usable when the measured no-load current value falls in a range of 0 to $M1$, as requiring maintenance when falls in a range of $M1$ to $M2$, and as being unusable when falls in a range over $M2$.

According to an example of the present method, said measuring in advance of no-load current values of a drive motor may be carried out with each of an increasing, direct drive, or reducing handpiece.

According to an example of the present method, the method may further include displaying on a display the determination made in the determining step.

According to the present invention, there is also provided a method for controlling a drive motor connected to a dental handpiece, said method comprising:

maintenance checking the handpiece according to the method of any one of claims 1 to 3, and when the handpiece is determined as requiring maintenance or being unusable, determining a limit of drive time of the drive motor with respect to the handpiece, and controlling operation of the drive motor based on said limit of the drive time to regulate revolution of the handpiece with respect to the drive time of the drive motor.

According to the present invention, there is further provided a system for carrying out the method for maintenance checking of a dental handpiece according to claim 1, said system comprising a dental handpiece according to claim 1, said system comprising a drive motor to which a dental handpiece to be checked is detachably attached, and a control system for controlling the operation of the drive motor, said control system further comprising:

a motor current detection unit for measuring a no-load current value of the drive motor, with a handpiece to be checked connected thereto and operated in no-load condition, a memory unit storing in advance, as reference data, no-load current values of the drive motor measured with a handpiece known as being in usable condition and a handpiece known as insufficiently maintained respectively connected thereto and operated in no-load condition, with associated data relating to degree of maintenance, and a computing unit for determining whether the handpiece checked is usable, requires maintenance, or is unusable, by comparing the measured no-load current value of the drive motor with said reference data.

According to an example of the present system, the no-load current value of the drive motor is measured by measuring, in the motor current detection unit, current value of the drive motor with a handpiece connected thereto and operated in no-load condition, and subtracting, in the computing unit, a current value of the drive motor measured alone without a handpiece connected thereto, from said current value of the drive motor measured with a handpiece connected thereto.

According to an example of the present system, the reference data stored in the memory unit further comprising a threshold M1 of the no-load current value up to which the handpiece is determined as usable, and a threshold M2 of the no-load current value beyond which the handpiece is determined as unusable, said thresholds M1 and M2 corresponding limits of an amount of heat generated by the handpiece with respect to the no-load current value of the drive motor measured in advance based on a relation therebetween, and wherein said computing unit determines the handpiece as being usable when the measured no-load current value falls in a range of 0 to M1, as requiring maintenance when falls in a range of M1 to M2, and as being unusable when falls in a range over M2.

According to an example of the present system, said motor current detection unit may be for measuring in advance no-load current value of a drive motor with each of an increasing, direct drive, or reducing handpiece.

According to an example of the present system, the control system may further comprise a display for receiving and displaying a determination from the computing unit.

According to the present invention, there is also provided a system for controlling a drive motor connected to a dental handpiece according to the method of claim 4, said system comprising the system of claim 5, wherein said computing unit, when determines the handpiece as requiring maintenance or being unusable, further determines a limit of drive time of the drive motor with respect to the handpiece, and wherein said motor control unit further controls operation of the drive motor based on said limit of the drive time to regulate revolution of the handpiece with respect to the drive time of the drive motor.

According to an example of the present invention, the control system may further comprise a motor control unit for controlling operation of the drive motor according to control signals received from the computing unit, said motor control unit having an integrating protection circuit for integrating a current value across the drive motor and a driven time, and a drive time protection circuit for regulating a limit of the drive time of the motor, wherein said motor control unit controls operation of the drive motor by means of he drive time protection circuit.

According to the present invention, the maintenance condition of a handpiece is deduced from the no-load current value of the motor to which the handpiece is connected, and the no-load current value is converted to a coefficient and used for controlling the drive motor so that the handpiece, if not usable, will not increase the load of the drive motor, to thereby prevent abnormal heat generation. Thus, even if an insufficiently maintained or unusable dental handpiece is used, the drive time of the drive motor is limited to prevent excess heat generation in the handpiece.

PREFERRED EMBODIMENTS OF THE INVENTION

The present invention will now be explained in detail with reference to FIGS. 1 to 8.

Figure 1:
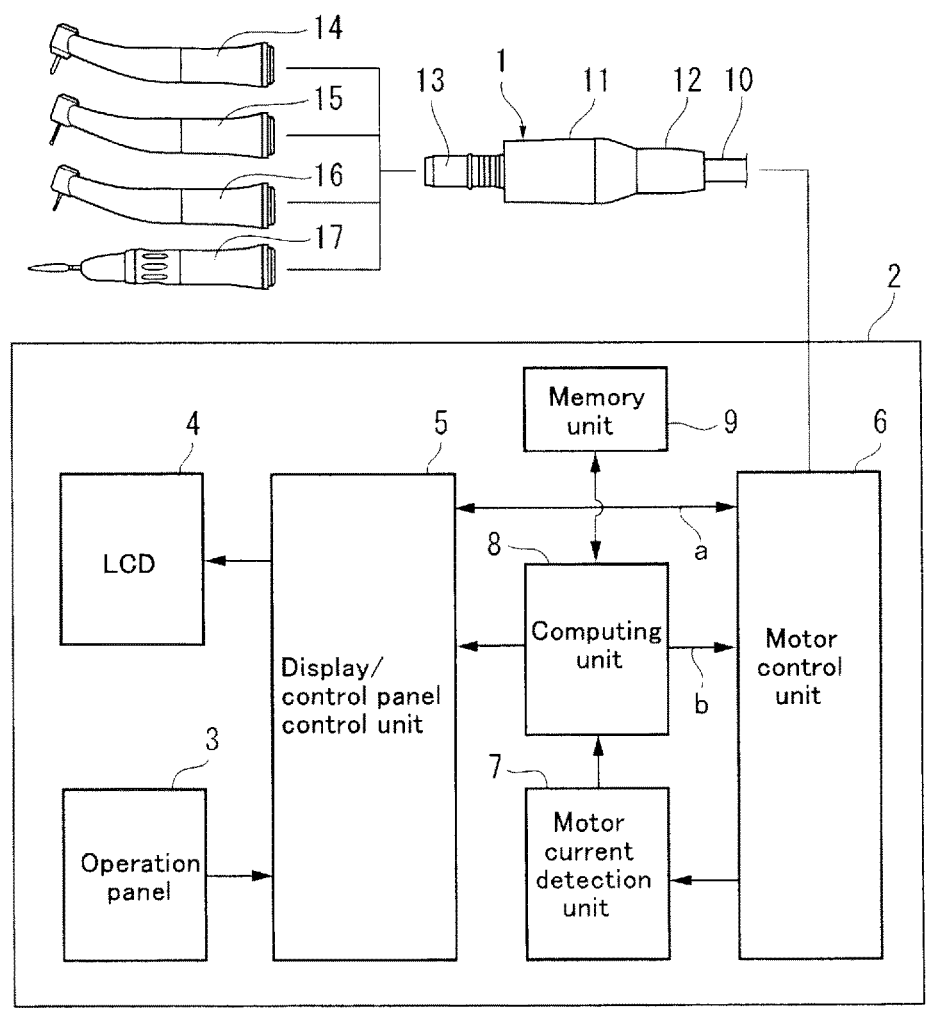
FIG. 1 is a block diagram illustrating an embodiment of the motor control system for a dental handpiece according to the present invention.

FIG. 1 is a block diagram illustrating an embodiment of the motor control system for a dental handpiece according to the present invention. The motor control system includes drive motor 1 and control system 2 for checking and controlling the motor 1.

The motor 1 has body 11, electrical cord connecting part 12 at the proximal end of the body 11, and handpiece coupling part 13 at the distal end of the body 11. To the electrical cord connecting part 12 is connected electrical cord 10 to provide electrical connection of the motor 1 to the control system 2, which is connected to a power source. To the handpiece coupling part 13, one of the various handpieces, e.g., contra-angle handpieces 14, 15, 16 and straight handpiece 17, is to be connected selectively. In this embodiment, the contra-angle handpiece 14 is a speed-increasing handpiece with the speed increasing ratio of 1:5 with respect to the revolution of the motor 1; the contra-angle handpiece 15 is a direct drive handpiece; the contra-angle handpiece 16 is a speed-reducing handpiece with the speed reducing ratio of 4:1 with respect to the revolution of the motor 1; and the straight handpiece 17 is a direct drive handpiece, like the contra-angle handpiece 15. In the description herein, one of these handpieces selectively connected to the handpiece coupling part 13 is comprehensively referred to as handpiece 14 for the sake of convenience, unless otherwise mentioned.

The control system 2 includes control panel 3 operating as an interface for inputting various operational directions (commands and the like), liquid crystal display (LCD) 4 for displaying checking items for the motor 1 and the results of the checking, display/control panel control unit 5 for controlling the control panel 3 and the LCD 4, motor control unit 6 connected to the motor 1 for transmitting and receiving control and current signals to and from the motor 1, motor current detection unit 7 connected to the motor control unit 6 for detecting current value of the motor 1, computing unit 8 for calculating the current value of the motor 1 based on the signals received from the motor current detection unit 7, and memory unit 9 connected to the computing unit 8 for storing various data required for operation of the control system 2.

Figure 2:
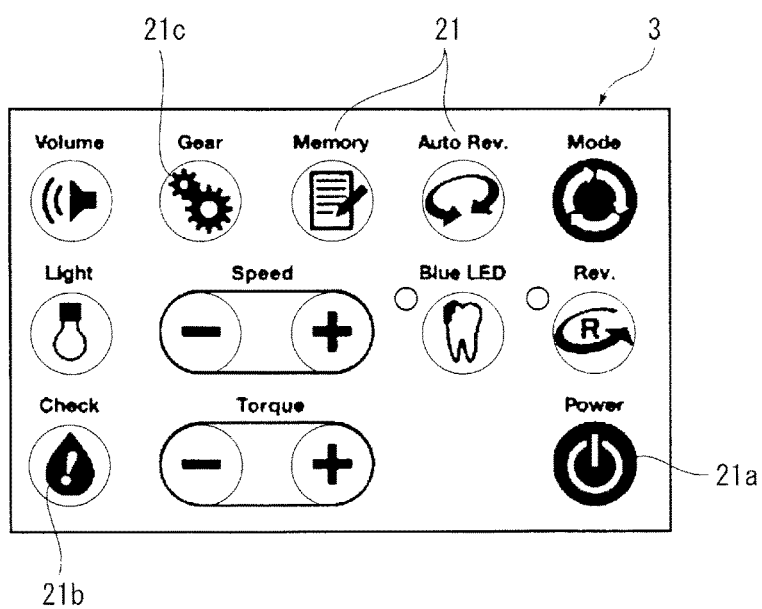
FIG. 2 shows an example of a control panel design for the control system according to the present invention.

The control panel 3 has a panel design exemplarily shown in FIG. 2. The control panel 3 has various iconic operation buttons 21 in the form of soft touch buttons. For example, button 21a is a power-on/off button, and button 21b is a "CONTRA-CHECK" button for commanding maintenance check of the handpiece 14. Button 21c is a gear ratio selection button for selecting the gear ratio of the handpiece. The remaining buttons shown in the figure have respectively assigned functions.

Figure 3:
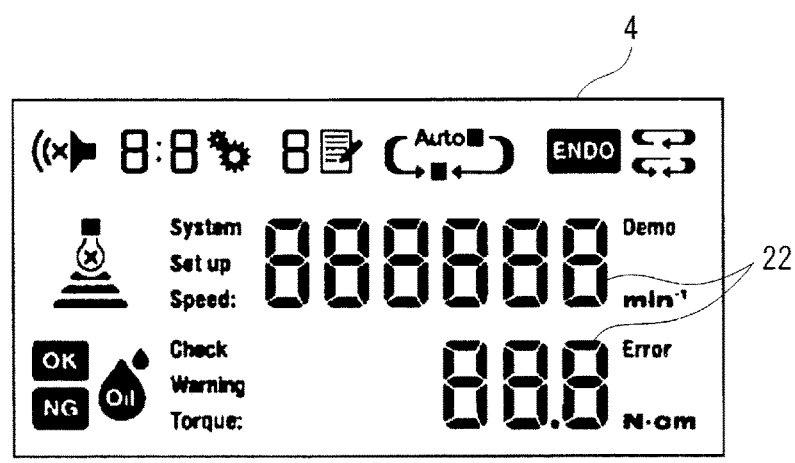
FIG. 3 is shows an example of a liquid crystal display design for the control system according to the present invention.

The LCD 4 has a screen design exemplarily shown in FIG. 3. The LCD 4 has various icons and data displays 22 for indicating, for example, check results of the handpiece 14 and the current value of the motor 1. The screen of the LCD 4 is switched in response to the selection of operations via the control panel 3.

The display/control panel control unit 5 is connected to the control panel 3, the LCD 4, and the computing unit 8 to transmit input data (operation command) received from the control panel 3 to the computing unit 8, or to transmit command data or display data received from the computing unit 8 to the control panel 3 or the LCD 4. The display/control panel control unit 5 is also connected to the motor control unit 6 via signal line a for directing the LCD 4 to display the no-load current value or the current value during the cutting operation of the motor 1.

The motor control unit 6 controls the operation of the motor 1 based on the current value of the motor 1 determined by the computing unit 8, and transmit the motor current value during operation of the motor 1 to the motor current detection unit 7 to determine the conditions of the motor 1. The motor current detection unit 7 receives signals from the motor control unit 6 to detect the motor current.

The motor control unit 6 and the motor current detection unit 7 together compose a motor current measurement unit.

The memory unit 9 is composed of memory means, for example, a hard disk drive (HDD), a read only memory (ROM), a random access memory (RAM), or a flash memory. The memory unit 9 stores various programs and data for the computing unit 8 to execute various processing, and various data generated or obtained by the computing unit 8 through various processing. The data to be used by the computing unit 8 for execution of various processing include data showing the relation between the no-load current value for the maintenance check and the result of determination.

The computing unit 8 is composed of, for example, a central processing unit (CPU), a random access memory (RAM) functioning as a main memory of the CPU, and a timer for controlling the clock-timing (e.g., 1 GHz) of processing. The computing unit 8 may partly be composed of a dedicated circuit, such as an application specific integrated circuit (ASIC). It is also conceivable that the computing unit 8 share the same CPU or main memory with the motor control unit 6, the motor current detection unit 7, and/or the memory unit 9.

Maintenance Check Processing (CONTRA-CHECK)

The operation of the motor control system having the above structure will be discussed.

The motor control system for a dental handpiece according to the present invention executes maintenance check processing, herein called "CONTRA-CHECK", to determine the maintenance conditions of the handpiece 14. The maintenance conditions of the handpiece 14 is determined by connecting the handpiece 14 to the handpiece coupling part 13 of the motor 1, energizing the motor 1 in the no-load state, and measuring the current value in this state. As defined hereinabove, "no-load" means that the dental tool attached to the handpiece 14 is not cutting anything and not loaded, so that only the gear transmission loss in the handpiece 14 is measured.

Figure 4:
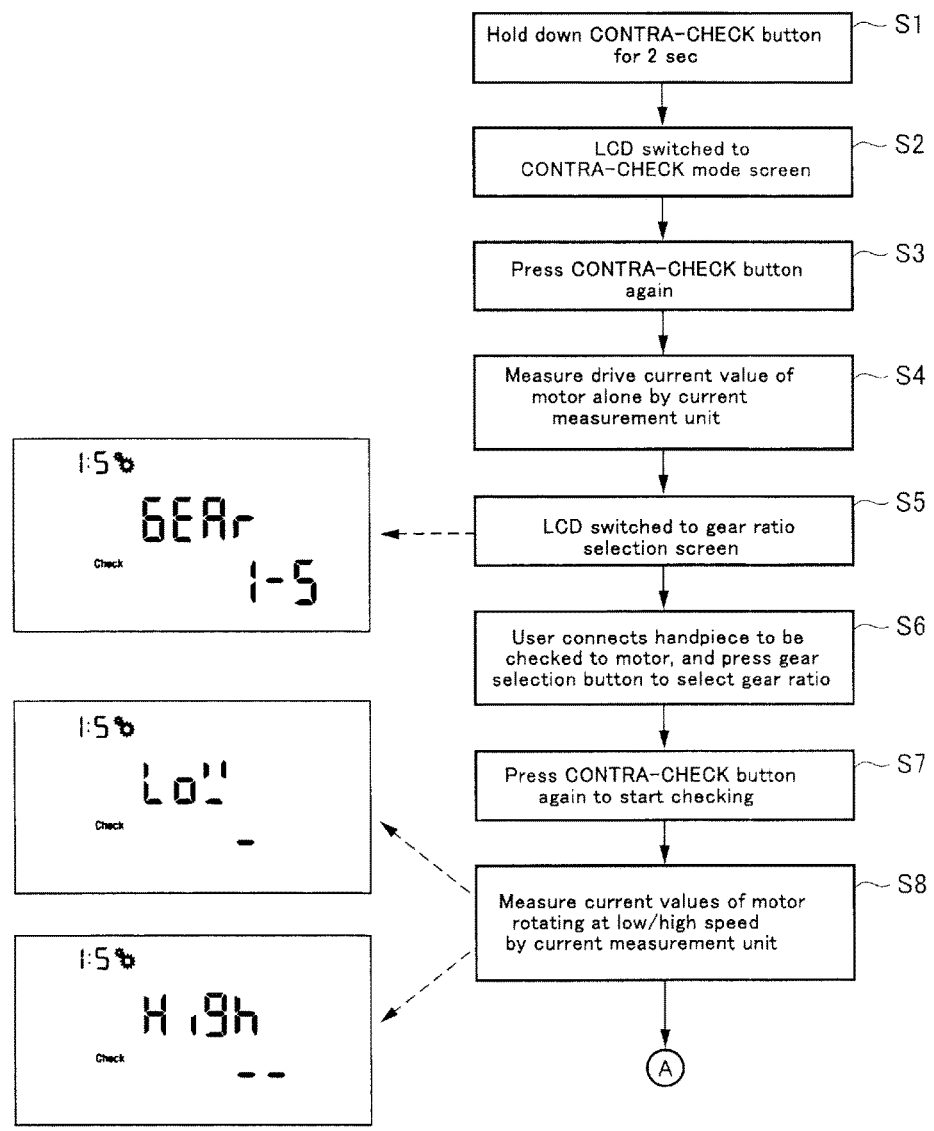
FIG. 4 is a flow chart illustrating the initial part of the maintenance check processing according to the present invention.
Figure 5:
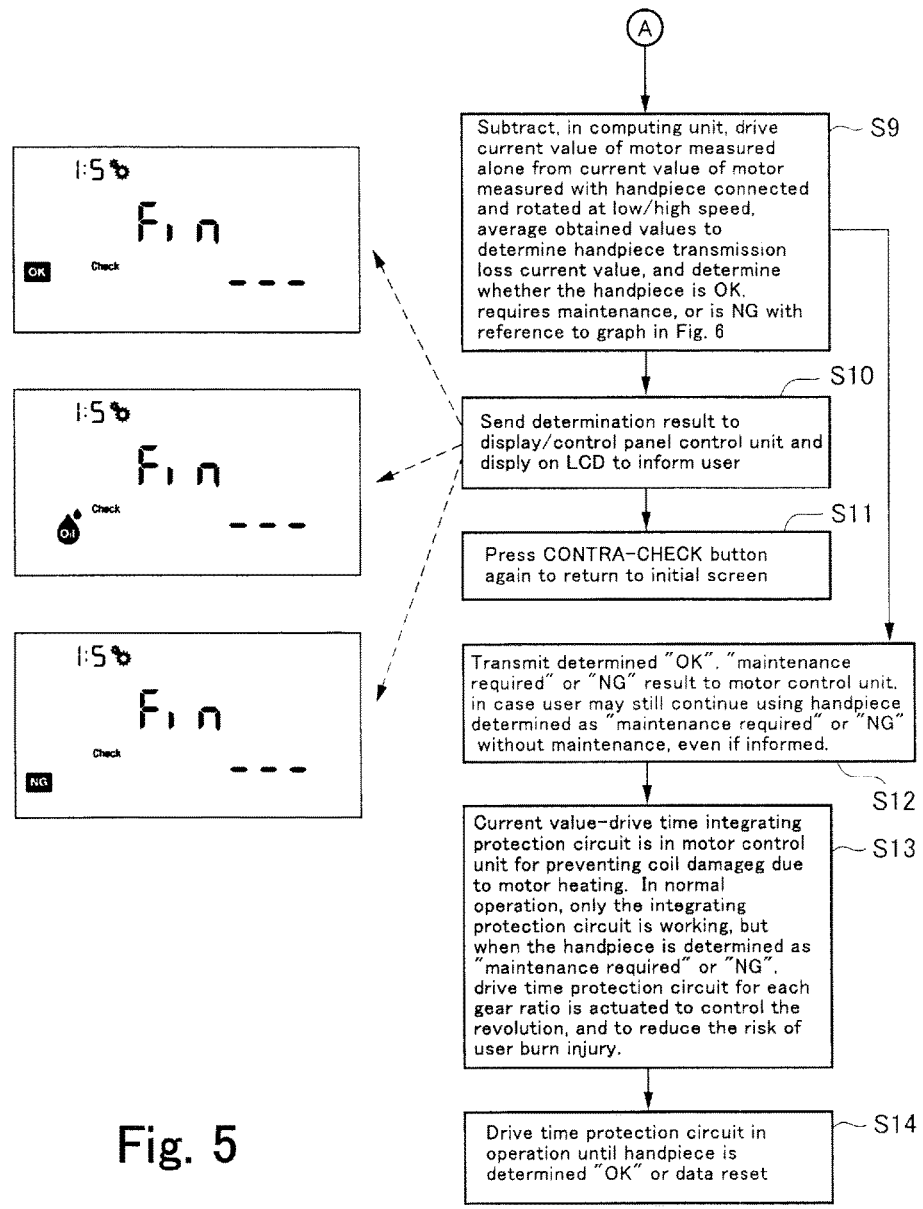
FIG. 5 is a flow chart illustrating the subsequent part of the maintenance check processing following FIG. 4 according to the present invention.

FIGS. 4 and 5 show the flow charts illustrating the CONTRA-CHECK processing. The user, e.g. a dentist, starts the CONTRA-CHECK processing by switching-on the CONTRA-CHECK by holding down the CONTRA-CHECK button 21b on the control panel 3 for two seconds (step S1). By this switching-on action, the LCD 4 is switched to the CONTRA-CHECK mode screen (step S2). When the CONTRA-CHECK button 21b on the control panel 3 is pressed again (step S3), the motor control unit 6 controls the motor 1 to rotate alone, and the current signal is transmitted from the motor control unit 6 to the motor current detection unit 7, wherein the driving current value of the motor 1 itself is measured, and the measured current value is stored in the memory unit 9 (step S4). Up to this point, the handpiece 14 is not connected to the handpiece coupling part 13 of the motor 1. Incidentally, step S4 of rotating the motor 1 alone and measuring the driving current value may be eliminated if the motor used is known to have little variation in its quality.

When the storage of the measured data is completed in S4, the LCD 4 is switched to the gear ratio selection screen (step S5). The user then connects a handpiece to be checked (here the handpiece 14) to the handpiece coupling part 13 of the motor 1, and presses the gear ratio selection button 21c on the control panel 3 to select the proper gear ratio (step S6). For example, when the handpiece 14 is connected to the motor 1, the gear ratio 1:5 is selected, whereas when the handpiece 15 is connected to the motor 1, the direct drive is selected. In FIG. 4, the display screen of the LCD 4 when the gear ratio of 1:5 is selected (showing 1:5, GEAr, and others)

is shown at the top of the left column, next to box S5. After the handpiece 14 is connected and the gear ratio is selected, when the user presses again the CONTRA-CHECK button 21b on the control panel 3, the checking process starts (step S7). During this checking, the motor 1 is rotated at a low speed and at a high speed under the control of the computing unit 8 and the motor control unit 6, and the respective current values are measured by the motor current detection unit 7 (step S8). Here, the rotation of the motor 1 and the measurement of the current values are carried out with the handpiece 14 in the no-load state, i.e., while the dental tool is not loaded, so that only the gear transmission loss in the handpiece 14 is measured. In FIG. 4, the display screens of the LCD 4 when the motor 1 is rotated at a low speed or at a high speed (1:5, Lo; or 1:5, High) are shown respectively in the middle and at the bottom of the left column, next to box S8.

When the current value measurements in S8 are completed, the computing unit 8 reads out from the memory unit 9 the stored driving current value of the motor 1 itself, subtracts this driving current value from the respective current values measured at low and high speeds with the handpiece 14 connected, and average the obtained values to obtain the transmission loss current value of the handpiece 14, which is taken as the no-load current value. That is, the "no-load current value" is the value of the current of the motor 1 derived from the gear transmission loss in the handpiece 14 when handpiece 14 is operated in the no-load condition. The computing unit 8 then determines from this no-load current value whether the handpiece is usable (OK), requires maintenance, or is unusable (NG) (step S9).

Incidentally, if the motor used is known to have little variation in rotation at low and high speeds, measurement at either low or high speed may suffice in S8. In this case, the value obtained by subtracting the driving current value from the current value measured either at low or high speed with the handpiece 14 connected is the no-load current value, i.e. the transmission loss current value of the handpiece 14.

Figure 6:
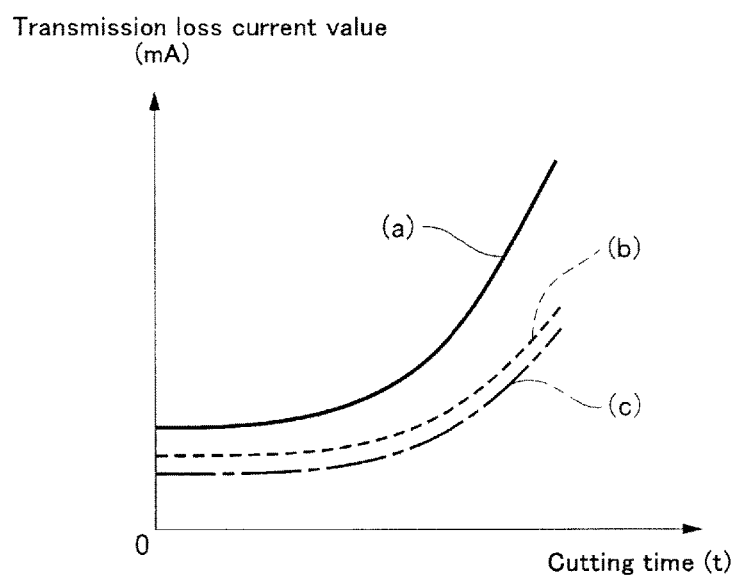
FIG. 6 is a graph showing the relation between the transmission loss current value and the cutting time of handpieces used in cutting without maintenance in the example.

FIG. 6 is a graph showing the relation between the cutting time (t) and the transmission loss current value (mA) of the handpiece 14 when continues cutting without maintenance. In the graph, curve (a) indicates the change of the handpiece transmission loss current value against cutting time in the contra-angle handpiece 14 (1:5 increasing), curve (b) indicates the change in the contra-angle handpiece 16 (4:1 reducing), and curve (c) indicates the change in the straight handpiece 17 (direct drive). The graph shows that the increasing ratio of the transmission loss current value of the handpiece is higher at a longer cutting time, and that the transmission loss current values of the 1:5 increasing handpiece 14 and the 4:1 reducing handpiece are higher than that of the direct drive handpiece 17.

Figure 7:
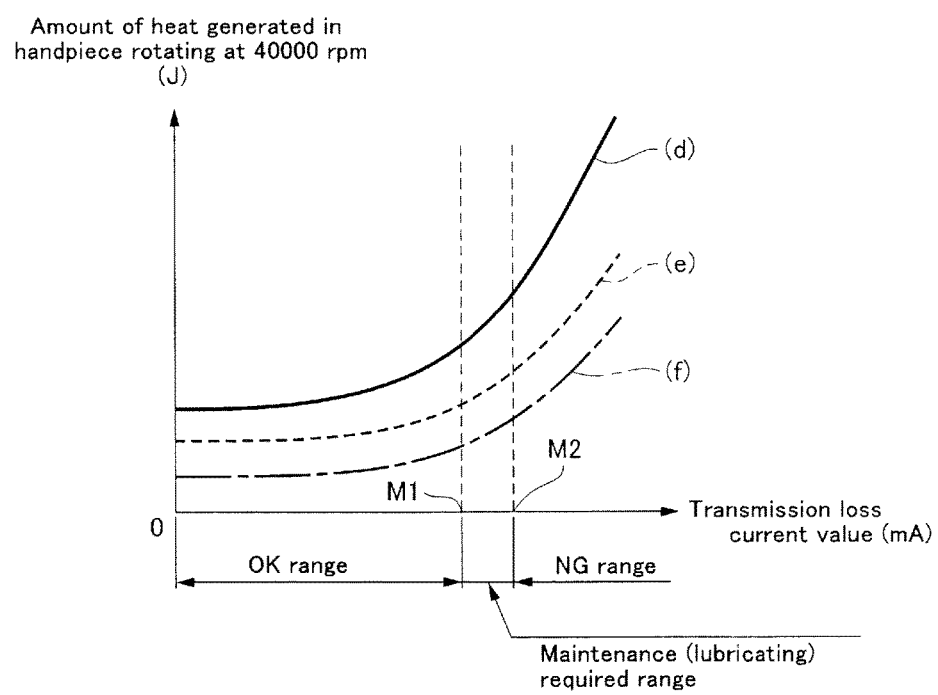
FIG. 7 is a graph showing the relation between the transfer loss current value and the amount of heat generated when the handpiece is operated.

FIG. 7 is a graph showing the relation between the transmission loss current value (mA) and the amount of heat generated by the handpiece rotated at 40,000 rpm, based on the graph in FIG. 6. In the graph, curve (d) indicates the change of the amount of heat against transmission loss current value in the contra-angle handpiece 14 (1:5 increasing), curve (e) indicates the change in the contra-angle handpiece 16 (4:1 reducing), and curve (f) indicates the change in the straight handpiece 17 (direct drive). The graph shows that the increasing ratio of the amount of heat generated by the handpiece is higher at a higher transmission loss current value, and that the amounts of heat generated by the 1:5 increasing handpiece 14 and the 4:1 reducing handpiece are larger than that generated by the direct drive handpiece 17.

The determination by the computing unit 8 in S9 is made based on the graphs in FIGS. 6 and 7. Specifically, the computing unit 8 finds out the bounds of the permissible amount of heat generated by the handpiece 14, decides thresholds M1 and M2 of the transmission loss current value (no-load current value), and sets the transmission loss current value range of 0 to M1 as the OK (usable) range, the range of M1 to M2 as the maintenance required range, and the range over M2 as the NG (unusable) range.

In the determination in S9, the present invention does not use the obtained no-load current value for torque correction. According to the present invention, the no-load current value of the motor 1 is measured in advance with each usable handpiece (standard handpiece for reference data collection) of 1:5 (increasing), 1:1 (direct drive), or 4:1 or 6:1 (reducing) gear ratio. From this value, the no-load current value based on which a handpiece of the same gear ratio is determined as usable, is determined and preset, together with the associated threshold M1, in the memory unit 9 of the control system 2 as reference data. On the other hand, the no-load current value of the motor 1 is also measured in advance with each handpiece of respective gear ratio undergoing insufficient maintenance (also standard handpiece for reference data collection). From this value, the no-load current value based on which a handpiece of the same gear ratio is determined as requiring maintenance, is determined and preset, together with the associated threshold M2, in the memory unit 9 as reference data. From the graphs in FIGS. 6 and 7, causal correlation is seen that insufficient maintenance results in generation of heat in the motor, which in turn results in greater friction loss in transmission between the gears, which in turn results in a higher no-load current value of the motor. Based on this, associated data, such as related equations, expressing that a higher no-load current value results in a higher amount of heat generation, are preset in the memory unit 9. The computing unit 8 compares the measured no-load current value for the selected handpiece 14, which is the object of the maintenance check, with the preset no-load current value to determine and output whether the handpiece 14 is "usable" (OK), "maintenance required", or "unusable" (NG).

The output determination result in S9 is transmitted to the display/control panel control unit 5, and displayed on the screen of the LCD 4 (step S10). In FIG. 5, examples of the display screen of the LCD 4 showing the determination results, "1:5, Fin, OK" (top), "1:5, Fin, Oil" (middle), or "1:5, Fin, NG" (bottom) are shown in the left column, next to box S10. The display thus informs the user of the determination result. Then, when the CONTRA-CHECK button 21b is pressed, the LCD 4 returns to the initial screen (step S11).

Motor Drive Control Processing

While transmitting the determination result of the CONTRA-CHECK to the display/control panel control unit 5 in S10, the computing unit 8 transmits the determination result also to the motor control unit 6 through the signal line b (step S12). This is for dealing with the possibility of the user to use the handpiece 14 determined as "maintenance required" or "NG" in S9, without maintenance, ignoring the information in S10. In order to protect the motor coil from being damaged by the heat generated by the motor 1, the motor control unit 6 has an integrating protection circuit for integrating the current value of the motor 1 and the driven time, and a drive time protection circuit for regulating the limit of the drive time of the motor 1. During the normal operation, only the integrating protection circuit is working in the motor control unit 6. When the maintenance check determines "maintenance required" or "NG", the drive time protection circuit for each gear ratio is actuated to control the revolution of the motor 1 with reference to the graph shown in FIG. 8 (to be discussed below), to thereby prevent overloading or heating of the motor 1 during operation of the handpiece 14 to reduce the risk of motor failure or other troubles (step S13). This motor control processing complements the maintenance check processing discussed above to establish a double safety system.

Figure 8:
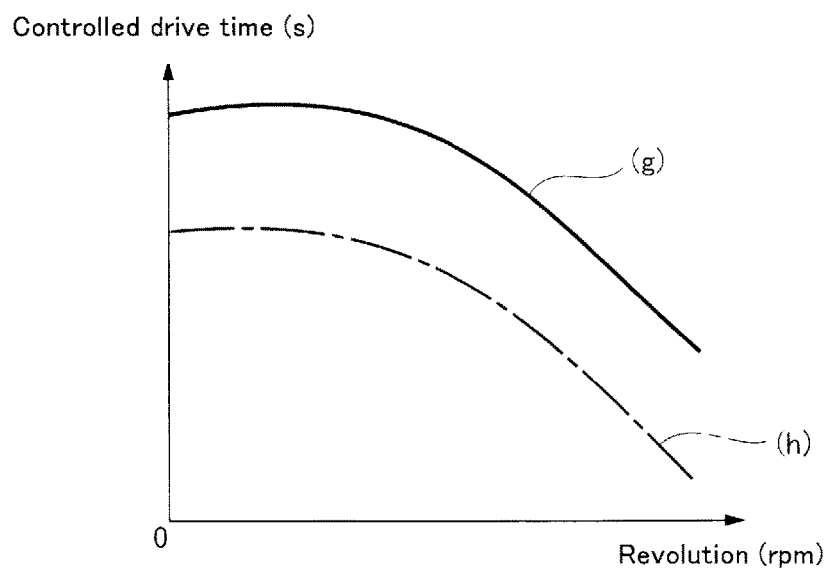
FIG. 8 is a graph showing the relation between the controlled drive time and the revolution of a contra-angle handpiece determined in the example.

FIG. 8 shows the relation between the controlled driven time (sec) and the revolution (rpm) of the contra-angle handpiece 14 (1:5 increasing). In the graph, curve (g) indicates the change of the controlled drive time against revolution in a handpiece falling within the "maintenance required" range, and curve (h) indicates the change in a handpiece falling within the "NG" range. In the drive control in S13, the computing unit 8 performs the calculation based on the graph in FIG. 8 to output motor control signals, and the motor control unit 6, based on the received motor control signals, controls the drive time of the motor 1 by means of the drive time protection circuit, so that when the handpiece 14 falling in the "maintenance required" range is continuously used without maintenance, a certain drive time is allowed, whereas when the handpiece falling in the "NG" range is continuously used without maintenance, the drive time is strictly regulated.

In the calculation, the computing unit 8 converts the no-load current value measured in the maintenance check processing to a coefficient (k), which is derived from the measured surface temperature and the measured no-load current value of a handpiece through experiments. The control system 2 controls the motor 1 using the revolution (r) of the handpiece 14, time (t), and the coefficient (k), as parameters relating to heat generation of the motor 1.

Through experiments, it is known that the surface temperature of a handpiece 14 is higher when the revolution (r) of the handpiece 14 is higher and the time (t) is longer, whereas the surface temperature of a handpiece 14 is not so high when the revolution (r) of the handpiece 14 is lower and the time (t) is shorter. The relation is also shown that a higher no-load current value (consequently, larger coefficient (k)) is associated with a larger transmission loss, which in turn is associated with a larger amount of heat generated. Thus, when limit (L) of the overall controlled drive time has been set as a motor system, the limit (L) is represented by the formula:

$$L \geq r \times t \times k$$

wherein L denotes the limit (sec) of the controlled drive time, r denotes the revolution (min$^{-1}$) of the handpiece, t denotes the time (sec), and k denotes the coefficient (min).

In driving the handpiece 14, the revolution and the controlled drive time of the handpiece 14 are regulated so as not to exceed the limit (L), and if the limit (L) is exceeded, the user is informed by, e.g., warning sound and screen flashing, that the handpiece 14 is generating heat and thus at risk. In case the user still does not stop the motor, the control system 2, by its control action, forced-stops the motor.

For example, the coefficient (k) for a handpiece determined as "OK" is 1, the coefficient k for a handpiece determined as "maintenance required" is 1.5, and the coefficient k for a handpiece determined as "NG" is 2. Coefficient k is larger when the no-load current value is larger, so that when the handpieces determined OK and NG are operated at the same revolution, the controlled drive time for the handpiece determined as NG is regulated to the half of the controlled drive time for the handpiece determined as OK.

The drive time protection circuit is operated until the computing unit 8 outputs the determination result "OK", or until the data is reset to the initial state, so that the drive time of the handpiece determined as "maintenance required" or "NG" is regulated (step S14).

In this way, operation of the overall motor control system for a dental handpiece is controlled by executing the maintenance check and the subsequent drive motor control.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A method for maintenance checking of, or controlling a drive motor connected to, a given dental handpiece, comprising:

measuring in advance no-load current values of the drive motor, with a first handpiece known as being in usable condition and a second handpiece known as insufficiently maintained respectively connected thereto and operated in no-load condition, storing as reference data said no-load current values of the drive motor together with associated data relating to degree of maintenance, measuring a further no-load current value of the drive motor with the given dental handpiece connected thereto and operated in no-load condition, and determining whether the given dental handpiece is usable, requires maintenance, or is unusable, by comparing the measured no-load current value with said reference data, wherein said reference data further comprises a threshold M1 of the no-load current value up to which the given dental handpiece is determined as usable, and a threshold M2 of the no-load current value beyond which the given dental handpiece is determined as unusable, said thresholds M1 and M2 corresponding to limits of an amount of heat generated by the given dental handpiece with respect to the no-load current value of the drive motor measured in advance based on a relation therebetween, and wherein in said determining, the given dental handpiece is determined as being usable when the measured no-load current value falls in a range of 0 to M1, as requiring maintenance when it falls in a range of M1 to M2, and as being unusable when it falls in a range over M2, and when the given dental handpiece is determined as requiring maintenance or being unusable, performing the maintenance on the given dental handpiece, determining a limit of drive time of the drive motor with respect to the given dental handpiece, and controlling operation of the drive motor based on said limit of the drive time to regulate revolution of the given dental handpiece with respect to the drive time of the drive motor, or opting not to use the given dental handpiece.

2. The method according to claim 1, wherein said no-load current values of the drive motor are each measured by measuring a first current value of the drive motor with the respective first, second or given dental handpiece connected thereto and operated in no-load condition, and subtracting a second current value of the drive motor measured alone without any handpiece connected thereto, from said first current value of the drive motor measured with the respective first, second or given dental handpiece connected thereto.

3. A system for carrying out the method for maintenance checking of, or controlling a drive motor connected to, the given dental handpiece according to claim 1, said system comprising the drive motor to which the given dental handpiece to be checked is detachably attached, and a control system for controlling the operation of the drive motor, said control system further comprising:

a motor current detection unit for measuring the further no-load current value of the drive motor, with the given dental handpiece to be checked connected thereto and operated in no-load condition, a memory unit storing in advance, as reference data, the no-load current values of the drive motor measured with the first handpiece known as being in usable condition and the second handpiece known as insufficiently maintained respectively connected thereto and operated in no-load condition, with associated data relating to degree of maintenance, and a computing unit for determining whether the given dental handpiece checked is usable, requires maintenance, or is unusable, by comparing the measured further no-load current value of the drive motor with said reference data, wherein said reference data stored in the memory unit further comprises a threshold M1 of the no-load current value up to which the given dental handpiece is determined as usable, and a threshold M2 of the no-load current value beyond which the given dental handpiece is determined as unusable, said thresholds M1 and M2 corresponding to limits of an amount of heat generated by the given dental handpiece with respect to the no-load current value of the drive motor measured in advance based on a relation therebetween, and wherein said computing unit determines the given dental handpiece as being usable when the measured no-load current value falls in a range of 0 to M1, as requiring maintenance when it falls in a range of M1 to M2, and as being unusable when it falls in a range over M2.

4. The system according to claim 3, wherein said no-load current values of the drive motor are each measured by measuring, in the motor current detection unit, a first current value of the drive motor with the respective first, second or given dental handpiece connected thereto and operated in no-load condition, and subtracting, in the computing unit, a second current value of the drive motor measured alone without any handpiece connected thereto, from said current first value of the drive motor measured with the respective first, second or given dental handpiece connected thereto.

* * * * *